United States Patent [19]

Cusato

[11] 4,035,919
[45] July 19, 1977

[54] DIRECT BONDING BRACKET POSITIONING AND MOUNTING TOOL
[75] Inventor: Anthony J. Cusato, Closter, N.J.
[73] Assignee: Dentronix, Inc., Trevose, Pa.
[21] Appl. No.: 693,008
[22] Filed: June 4, 1976
[51] Int. Cl.² ............................................. A61C 7/00
[52] U.S. Cl. ..................................................... 32/66
[58] Field of Search .................. 32/14 A, 14 B, 14 C, 32/14 D, 14 E, 66, 40 R

[56] References Cited
U.S. PATENT DOCUMENTS

| 3,686,762 | 8/1972 | Sutter | 32/66 |
| 3,871,098 | 3/1975 | Dean | 32/66 |

Primary Examiner—Robert Peshock
Attorney, Agent, or Firm—Ralph R. Roberts

[57] ABSTRACT

This invention pertains to a direct bonding bracket positioning tool for orthodontists. A tweezer-type tool has the end of an outer jaw and an intermediate jaw configured and sized to receive and retain a cement-attached bracket as the bracket is directly bonded to the face of the tooth of the patient. For precise positioning of the bracket on the tooth there is provided a screw which is adjusted to position an extending jaw end, which is a third jaw, at a selected distance above the intermediate bracket retaining ends of the three jaw tweezer. This arrangement of jaw ends is depicted in two versions for the two most popular brackets in use. The adjustable top jaw is used to hold the gripped bracket in the selected position as and during the hardening of the bonding agent.

10 Claims, 6 Drawing Figures

DIRECT BONDING BRACKET POSITIONING AND MOUNTING TOOL

BACKGROUND OF THE INVENTION

1. Field of the Invention

With reference to the classification of art as established in the United States Patent & Trademark Office the present invention pertains to the Class generally identified as "Dentistry" (class 33) and more particularly to the subclass of "instruments- orthodontic" (subclass 66).

2. Description of the Prior Art

The widespread use of direct bonded brackets by orthodontists to hold wire to and on the teeth of a patient is a rather recent development. Plastic and/or metal brackets are attached to the tooth of the patient by an appropriate cement. This cement must harden when and while the bracket is held fixedly in place against the tooth. Tweezers of all shapes and description are known and employed by orthodontists in the pursuit of their treatments but, insofar as is known, it is new and novel to provide a bracket placing and holding tool whereat a direct bonding bracket is gripped by the front portion of two jaws and with adjustable means a third jaw end is positioned so as to work in a determined relationship to the two holding ends of the tweezer. This third jaw end is adjusted as to its distance from the middle jaw and in bracket placing position rests upon the top of the tooth to precisely position the bracket as it is directly bonded to the tooth.

Tweezers and pliers having small jaw ends are well known. These may and have been used to grasp the direct bonding bracket as they are held in position for the hardening of the cement by which the bracket is secured to the tooth. Because of the difficulty of placing and holding the to be, bonded bracket without involuntary hand movement as well as alignment during the initial application, unsatisfactory placement and bonding often occurs. In combination with the adjustable setting means there is also provided a scale by which the desired positioning may be pre-established. This setting precisely positions the bracket in relation to the top of the tooth to which the bracket is secured. During the cement hardening period the extending jaw rests lightly on top of the tooth to which the bracket is mounted.

SUMMARY OF THE INVENTION

This invention may be summarized at least in part with reference to its objects.

It is an object of this invention to provide, and it does provide a bracket holding tool or instrument which retains a direct bonding bracket on the tip end of two jaws carried by the same leg of a tweezer-type tool. The other leg has an extending jaw portion which is adapted to rest on the top of a tooth as the direct bonded bracket is attached to the face of the tooth. A screw is adjustably carried in the top leg of the tweezer to selectively position the gripped bracket in relation to the extending jaw end.

This tool or instrument is generally a tweezer having two legs joined at one end and by the construction of the legs they are urged toward one another. To one of the legs which for the purposes of identification is called the upper leg, there is attached to the inside of this leg a third leg member which is of a short length and is constructed so as to lay adjacent the inside or top surface of the lower leg. The outer end of the lower jaw is L-shaped with the short leg adapted to slidably enter and be retained in a lower groove for wire as provided and formed in the bracket. This L-shaped end cooperates with a short blade-like jaw carried by and on the inside of the upper jaw or leg. This short jaw is sufficiently thin at least at its outer end so as to easily enter a wire retaining groove formed on the front of the bracket. A residual bias is provided so that when a bracket is positioned between the L-shaped lower jaw and the middle blade-like member the bracket is gripped in a determined and precise relationship.

The top leg of the tool has its tip end extending sufficiently so that at least one-eighth inch or more extends beyond the rear face of the bracket to be mounted when this bracket is gripped by the L-shaped lower jaw and intermediate blade end. An adjusting screw is carried by the upper jaw and is rotated so as to precisely space the upper jaw from the middle blade. A scale may be provided by which the upper jaw is precisely positioned in relation to the middle blade.

In addition to the above summary the following disclosure is detailed to insure adequacy and aid in understanding of the invention. This disclosure, however, is not intended to cover each new inventive concept no matter how it may later be disguised by variations in form or additions of further improvements. For this reason there has been chosen specific embodiments of the direct bonding bracket positioning tool as adopted for use with plastic and metal brackets attached by direct bonding and showing a preferred means for construction and use. These specific embodiments have been chosen for the purposes of illustration and description as shown in the accompanying drawing wherein:

BRIEF DESCRIPTION OF THE DRAWING

In the following description and in the claims various details will be identified by specific names for convenience; these names, however, are intended to be generic in their application. Corresponding reference characters refer to like members throughout the six figures of the drawing.

This drawing accompanying, and forming part of, this specification discloses certain details of construction for the purpose of explanation but it should be understood that these details may be modified without departure from the concept of the invention and that the invention may be incorporated in other structural forms than shown.

DESCRIPTION OF THE GENERAL ARRANGEMENT OF FIGS. 1 AND 2

Figure 1:
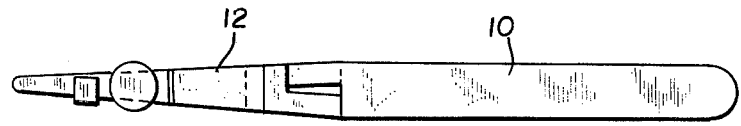
FIG. 1 represents a plan view of the tweezer-type direct bonding bracket holding and positioning tool of this invention and shown substantially full scale.
Figure 2:
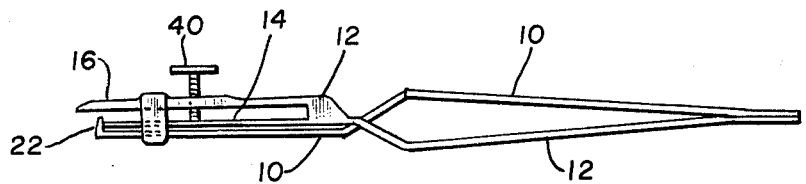
FIG. 2 represents a side view of the tool or instrument of FIG. 1.

Referring to the drawing and in particular to FIGS. 1 and 2, there is depicted a tweezer having very similar leg portions 10 and 12. These leg portions are fastened at their left ends in a common joint. The tweezer legs are formed so that as assembled the jaw ends move toward and to each other. A cut-out portion near midlength permits the jaw members to pass by each other in an X-type pattern. For the sake of identification the lower leg portion at the left end of FIG. 2 is called the lower leg. To the upper leg and at about one and a quarter inches from the left end of the jaw end is secured an intermediate jaw member identified as 14. The intermediate jaw, as shown, is attached to the upper jaw. For manufacturing convenience this intermediate jaw is made as a part of the jaw member. The intermediate jaw, as depicted, is a part of the uppr jaw stamping and is bent to the configuration shown. When the jaws 10 and 12 are released the intermediate jaw lays or reposes next to the inside surface of the lower jaw 10. The intermediate member 14 is rather thin and its left end has a thickness which is a sliding fit in a center slot in a bracket.

Figure 3:
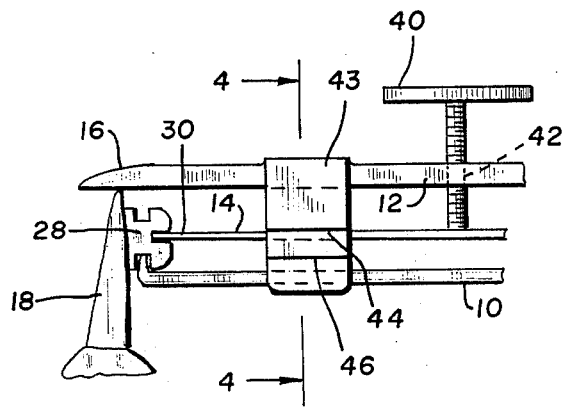
FIG. 3 represents a fragmentary side view in an enlarged scale of the jaw end of the tool as in FIG. 2 and particularly showing the construction wherein the middle jaw is a thin blade-like member.
Figure 5:
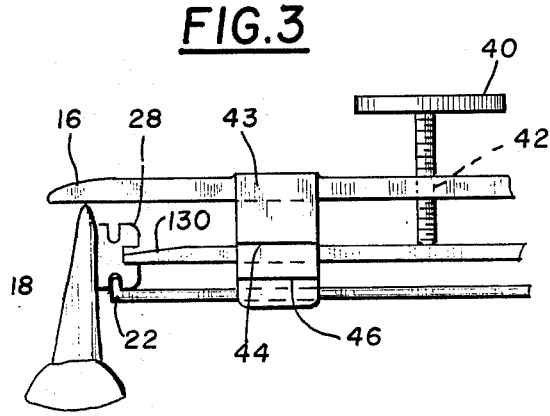
FIG. 5 is a fragmentary side view of the tool as in FIG. 3 but in which the middle jaw member is made of a thicker material and the outer end is reduced in thickness to provide an easy entry and withdrawal from the midwire groove or slot in the bracket.

The upper jaw 12 is made the same or similar in all models, to be hereinafter discussed. The extending end 16 of the upper jaw is intended to extend beyond the lower jaw portions and in use this extending portion rests upon the top of a tooth 18, as seen in FIGS. 3 and 5. For aesthetic reasons and so that the end of this extending end 16 does not cut or scratch the patient's mouth, sharp edges on this extending jaw portion are removed. The lower jaw 10 has its outer end formed with an L-shape 22. The upwardly turned end is made sufficiently thin and of a length which is adaptable for easy entry into and withdrawal from the lower groove of a bracket.

DESCRIPTION OF THE SPECIFIC JAW ENDS AS SEEN IN FIGS. 3 THROUGH 6

Figure 6:
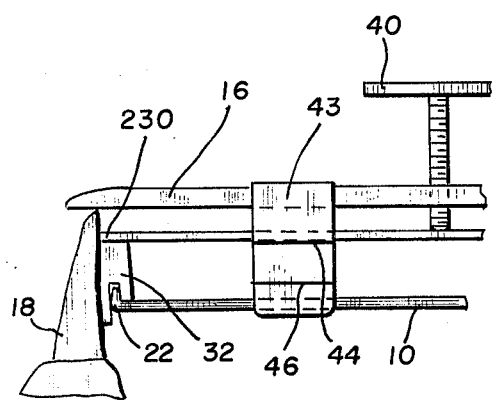
FIG. 6 represents the jaw ends of the tool as in FIG. 3 but with the middle jaw made slightly longer to rest upon and grasp the upper surface of an edgewise bracket.

Referring to the drawing and to the specific embodiments shown in FIGS. 3 through 6, it is noted that in FIGS. 3, 5 and 6 the upper jaw end 16 is shown substantially identical in all embodiments. The lower jaw end and its L-shap 22 are also contemplated to be substantially identical in all embodiments. The upturned end is toward the extended end of the upper jaw. The upturned end has its end surface parallel to the support surface 24 provided by the inside surface of the jaw. Two forms of brackets are depicted. A very popular bracket is the edgewise bracket of FIGS. 3 and 5 which has grooves both at the top and bottom and also midway of the front. This bracket is identified as 28. A narrow blade end 30 of the intermediate jaw or leg 14 enters the mid-groove on the bracket 28 and with the natural spring or bias provided by the deliberately formed lower and intermediate jaw members causes a movement of the intermediate jaw member toward the lower leg between which the bracket 28 is retained by the L-shaped end 22 and the blade end 30 as they are positioned in appropriate grooves. It is to be noted in FIGS. 3 and 5 that the end 30 of the intermediate jaw does not extend beyond the inside of the L-shape 22.

Figure 4:
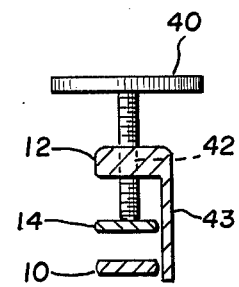
FIG. 4 represents a sectional view taken on the line 4—4 of FIG. 3 and looking in the direction of the arrows.

In FIG. 5 the intermediate jaw, instead of the conventionally thin member of FIGS. 3 and 4, is made a little heavier and the outer end is tapered so that the entering end easily enters the groove in the bracket 28. For the purpose of identification this intermediate blade of FIG. 5 is noted as 114 and the tapered end is noted as 130.

In FIG. 6 the thin blade 14 may be the same length as in FIG. 3 but if desired may be as long as the end of the upwardly extending L-shape 22 on the lower leg. The bracket illustrated in this FIG. 6 is called the light wire bracket (Begg) and for identification is numbered 32. This extended middle jaw end in FIG. 6 is identified as 230. The L-shaped lower jaw retaining end 22 acts as in the above-noted embodiments while the longer middle jaw end identified as 230 in bracket retaining condition rests on the top flat surface of the light wire bracket 32.

ADJUSTABLE PRECISION SETTING OF BRACKET

Whether the bracket 28 of FIGS. 3 and 5 or the bracket 32 of FIG. 6 is to be mounted on the tooth 18 of a patient it is comtemplated that a precision setting means will be provided. This setting means is adapted for setting before insertion of the bracket into the jaw ends of the tool. The precision setting means includes a thumb wheel 40 which has a large diameter head portion and a threaded stem. The threaded stem is carried by a threaded aperture 42 in the upper leg member 12. In combination with this screw adjustment there is carried on the top jaw member a setting scale 43 which preferably has setting or indicating lines 44 and 46. These lines indicate usual settings for the top or bottom edge of the intermediate jaw member. As seen in FIGS. 3 and 5, the top indicating line 44 is more-or-less in coincidence with the top surface of the intermediate jaw. In FIG. 6 the top line 44 is more-or-less in coincidence with the bottom surface of the jaw member 230. As the intermediate jaw is carried and is movable with the upper jaw the screw setting can be made and left in the adjusted position during all the mounting actions of the bracket into the jaw ends, as depicted.

USE AND OPERATION

As constructed the tweezer legs 10 and 12 of this invention are configured to be assembled at their right ends, as seen in FIGS. 1 and 2. When brought together and assembled the left jaw ends are naturally biased toward each other. Grasping the midportions of the legs and moving them toward each other separates the jaw ends from each other. In order to insert a bracket the midportion of the legs 10 and 12 are grasped and moved toward one another. The lower jaw end 22 moves away from the intermediate jaw as carried by the upper leg and in the manipulated space derived by spacing the legs 10 and 12 the bracket is moved between the L-shaped end 22 to move or be positioned in the lower groove of the bracket 28. The intermediate jaw end 30 or 130 is then moved into the mid-groove of the bracket and the legs 10 and 12 are then released for gripping the bracket. The bias for gripping the bracket is made rather low so that undue pressure on the bracket is not provided in the tweezers. Once the bracket is retained in position on the jaw ends of the tool the orthodontist manipulates the screw 40 to cause the upper extending jaw portion 16 to be brought to a desired position. This may be set or preset by using the indicating lines 44 and 46 upon the gauge or scale member 43 to preposition the end of the intermediate jaw as far as its relationship to the upper extending jaw 16.

Where the light wire bracket of FIG. 6 is to be used, the thin jaw member 230 is brought to the top of and positioned on the top surface of the bracket 32 and the L-shaped jaw end 22 of the lower jaw is brought into the groove of this bracket. Between these two jaw end portions the bracket is retained by the residual spring or bias in the two leg members 10 and 12. The screw 40 ins manipulated to cause the jaw resting extending portion 16 to be brought to the desired relationship with the bracket so that when positioned on te tooth 18 a precise setting will be obtained.

When and as the brackets 28 and 32 are to be applied to the tooth 18, te bonding cement is applied either to the tooth or to the bracket in a conventional manner and then with the bracket mounted in the tool the extending jaw portion 16 is brought to the top of the tooth 18. The bracket is now pressed against the face of the tooth and held in this position with the jaw 16 resting upon the top of the tooth until the setting of the cement has been achieved. When this has been accomplished and the bracket has been adhered to the tooth, the tool is removed by grasping the midportion of the legs 10 and 12 and moving the jaw ends apart. The L-shaped end moves from the lower groove and by a withdrawing or sideways movement the end of the intermediate jaw is removed from the midgroove of the bracket 28. With a bracket 32 the same procedure is followed but the intermediate jaw is not in a groove.

The orthodontist may check the positioning of the bracket before the applying of the cement to the tooth. If he wishes, he can compare the setting of the to be mounted bracket with a bracket mounted upon an adjacent tooth and by manipulating the screw 40 may position the gripped bracket to be moved up and down in relation to the supporting jaw 16.

The tool to hold and position the bracket for direct bonding employs a simple tweezer construction with the free ends normally urged toward each other. A cross-over construction of the legs at their midlength enables the user of the tool to grasp the legs at a convenient position and press the midportions toward each other to open the jaw ends. The lower L-shaped end 22 is moved from a gripping condition with the intermeditate leg and jaw end by the squeezing manipulation of the legs 10 and 12. Other arrangements may provide the same basic concept and requirement but as long as a direct bonding bracket is engaged by a jaw end which enters a lower groove and an intermediate jaw end which cooperates with the lower jaw to grip the bracket the essential releasable holding of the bracket is accomplished. An extending upper jaw end rests upon the top of the tooth during positioning and setting of the cement. This setting is accomplished by the screw means of this invention but other forms of setting employing other than a rotating screw may be provided. Such alternates include a tapered wedge-type slide, ratchet wheels and the like.

Terms such as "left", "right", "up", "down", "bottom", "top", "front", "back", "in", "out", and the like are applicable to the embodiments shown and described in conjunction with the drawing. These terms are merely for the purposes of description and do not necessarily apply to the position in which the orthodontic tool for positioning and holding a direct bonded bracket may be constructed or used.

While particular embodiments of the tweezer-type tool and alternate embodiments have been shown and described it is to be understood the invention is not limited thereto since modifications may be made within the scope of the accompanying claims and protection is sought to the broadest extent the prior art allows.

What is claimed is:

1. An orthodontic tool particularly for positioning and holding a direct bonding bracket as it is positioned while permitting adhering cement applied thereto to harden to secure the bracket to a tooth of a patient, said tool including: (a) a tweezer-type tool having upper and lower leg members attached at one end and as assembled there is a constructed bias so that the unconnected leg ends are movable toward and to each other; (b) an intermediate leg member carried between the upper and lower leg members and as constructed and assembled a bias is provided to urge the lower leg toward the intermediate leg, the ends of the lower leg and the intermediate leg disposed to cooperatively retain a direct bonded bracket positioned therebetween; (c) an extending jaw portion provided on the upper leg member and providing therewith a means for supporting the tool on the top of a patient's tooth as the bracket is positioned and the applied cement hardens securing the bonded bracket to the tooth; (d) a lower jaw end carried by and formed on the free end of the lower leg member, this jaw end being L-shaped and with the short portion of the L-shape extending toward the extending upper jaw, this short leg sufficient to slidably engage and enter a lower slot formed on the direct bonded bracket, and (e) adjusting means cooperatively carried by the upper and intermediate leg members whereby the intermediate leg end is positioned a selected distance from the underside of the extending upper jaw, whereby the upper and lower legs are moved by manual manipulation from each other and to open condition whereby the lower and intermediate jaw ends are sufficiently opened to place a direct bonding bracket therebetween and in a holding position whereat the legs are released to grip the bracket by the ends of the lower and intermediate legs and while gripped the adjustment means is moved as required to being the bracket to the desired position below the upper jaw.

2. An orthodontic tool for positioning and holding a direct bonded bracket as in claim 1 in which the tweezer legs are formed and are assembled to provide an X-type cross-over assembly.

3. An orthodontic tool for positioning and holding a direct bonded bracket as in claim 1 in which the intermediate leg is carried by and is movable with the upper leg.

4. An orthodontic tool for positioning and holding a direct bonded bracket as in claim 3 in which the intermediate leg is a thin blade whose end as it extends toward the free end is less than the inside extent of the short leg of the L-shaped lower leg.

5. An orthodontic tool for positioning and holding a direct bonded bracket as in claim 3 in which the intermediate leg is blade-like with the outer end thinned so as to easily enter a wire slot as formed in the midportion of a direct bonded bracket.

6. An orthodontic tool for positioning and holding a direct bonded bracket as in claim 5 in which the intermediate leg has its free end of an extent which is less than the inside extent of the short leg of the L-shaped lower leg.

7. An orthodontic tool for positioning and holding a direct bonded bracket as in claim 3 in which the intermediate leg is a thin blade whose free end extends at least to the inside edge of the upturned jaw end of the L-shaped lower leg so that and when this intermediate jaw is placed on the top surface of a light wire bracket it provides a full pressing action on the bracket.

8. An orthodontic tool for positioning and holding a direct bonded bracket as in claim 3 in which the adjusting means includes a thumb screw carried in a threaded aperture in the top leg and with the end of the screw extending into the space between the top and intermediate legs to engage the top surface of the intermediate leg and by the manipulation of the screw to move the intermediate leg against the residual bias to bring the intermediate leg into a selected position with respect to the undersurface of the extending top leg.

9. An orthodontic tool for positioning and holding a direct bonded bracket as in claim 2 in which there is provided a setting scale which is cooperatively carried so that indicia on said scale indicates the positioning of one of the surfaces of the intermediate member in relation to the position of the undersurface of the extending jaw of the upper leg.

10. An orthodontic tool for positioning and holding a direct bonded bracket as in claim 9 in which the setting scale is attached to and is movable with the upper leg.

* * * * *